(12) United States Patent
Harrison et al.

(10) Patent No.: US 11,458,279 B2
(45) Date of Patent: Oct. 4, 2022

(54) SLEEP ENHANCEMENT SYSTEM AND WEARABLE DEVICE FOR USE THEREWITH

(71) Applicant: Thought Beanie Limited, Bristol (GB)

(72) Inventors: Simon Harrison, Bristol (GB); Alyn Morgan, Bristol (GB)

(73) Assignee: Thought Beanie Limited, Bristol (GB)

( * ) Notice: Subject to any disclaimer, the term of this patent is extended or adjusted under 35 U.S.C. 154(b) by 168 days.

(21) Appl. No.: 16/757,609

(22) PCT Filed: Oct. 19, 2018

(86) PCT No.: PCT/EP2018/078739
§ 371 (c)(1),
(2) Date: Apr. 20, 2020

(87) PCT Pub. No.: WO2019/077120
PCT Pub. Date: Apr. 25, 2019

(65) Prior Publication Data
US 2020/0261689 A1    Aug. 20, 2020

(30) Foreign Application Priority Data
Oct. 20, 2017 (GB) ..................... 1717311

(51) Int. Cl.
*A61M 21/02* (2006.01)
*A61B 5/00* (2006.01)
(Continued)

(52) U.S. Cl.
CPC ............. *A61M 21/02* (2013.01); *A61B 5/316* (2021.01); *A61B 5/369* (2021.01); *A61B 5/4815* (2013.01);
(Continued)

(58) Field of Classification Search
CPC ..... A61B 5/7267; A61B 5/4812; A61B 5/721; A61B 2560/0425; A61B 2562/0219;
(Continued)

(56) References Cited

U.S. PATENT DOCUMENTS

2011/0267196 A1* 11/2011 Hu ..................... A61B 5/681
340/575
2013/0303837 A1    11/2013 Berka et al.
(Continued)

FOREIGN PATENT DOCUMENTS

| CN | 102247122 A | 11/2011 |
|----|-------------|---------|
| WO | 2014/118650 A1 | 7/2014 |

(Continued)

OTHER PUBLICATIONS

International Search Report and Written Opinion issued in corresponding International Patent Application No. PCT/EP2018/078739 dated Dec. 19, 2018.
(Continued)

*Primary Examiner* — Christine H Matthews
*Assistant Examiner* — Joshua Daryl D Lannu
(74) *Attorney, Agent, or Firm* — Troutman Pepper Hamilton Sanders LLP (57) ABSTRACT

A system in which a wearable device detects an electroencephalographic (EEG) response from a user during sleep-related activity, e.g. trying to fall asleep, being asleep or waking up, and outputs an audio signal that is tailored, based on the EEG response, to enhance the user's sleep experience. In particular, an audio, thermal and/or olfactory signal may be used to facilitate any one or more of (i) a smooth path into REM sleep, (ii) a reduced potential for sleep being disturbed, and (iii) exit from sleep at an optimum time. In one example, the system synchronizes properties of an audio signal comprising a dominant white and/or pink noise com- (Continued)

ponent with the identified sleep-related parameters. The synchronized properties can include any of intensity, frequency, tone, volume and rhythm.

17 Claims, 6 Drawing Sheets

(51) Int. Cl.
    *A61M 21/00*     (2006.01)
    *A61B 5/316*     (2021.01)
    *A61B 5/369*     (2021.01)

(52) U.S. Cl.
    CPC ............. *A61B 5/6803* (2013.01); *A61B 5/721* (2013.01); *A61B 5/7267* (2013.01); *A61B 2562/0219* (2013.01); *A61M 2021/0027* (2013.01); *A61M 2205/3303* (2013.01); *A61M 2209/088* (2013.01); *A61M 2230/10* (2013.01)

(58) Field of Classification Search
    CPC .......... A61B 5/7246; A61B 2560/0468; A61B 5/369; A61B 5/6831; A61B 5/7264; A61B 5/6815; A61B 5/316; A61B 5/0006; A61B 5/4815; A61B 5/6814; A61B 5/6803; A61B 5/375; A61B 2562/164; A61B 5/30; A61B 5/7405; G16H 50/20; A61M 21/02; A61M 2209/088; A61M 2205/3303; A61M 2021/0027; A61M 2230/10
See application file for complete search history.

(56) References Cited

U.S. PATENT DOCUMENTS

| | | | |
|---|---|---|---|
| 2014/0221779 A1 | 8/2014 | Schoonover et al. | |
| 2014/0378808 A1* | 12/2014 | Lee | A61B 5/6803 600/383 |
| 2015/0297109 A1 | 10/2015 | Garten et al. | |
| 2016/0082222 A1* | 3/2016 | Garcia Molina | A61B 5/375 600/27 |
| 2017/0270810 A1* | 9/2017 | Imran | A61B 5/4812 |
| 2018/0160982 A1* | 6/2018 | Laszlo | A61B 5/7225 |
| 2018/0236232 A1* | 8/2018 | Soulet De Brugiere | A61B 5/38 |

FOREIGN PATENT DOCUMENTS

| | | | | |
|---|---|---|---|---|
| WO | 2016/083929 A1 | 6/2016 | | |
| WO | 2016/166202 A1 | 10/2016 | | |
| WO | 2017/021662 A1 | 2/2017 | | |
| WO | WO-2017021662 A1 * | 2/2017 | ........... | A61B 5/6814 |

OTHER PUBLICATIONS

Patents Act 1977: Search Report under Section 17(5) issued in corresponding United Kingdom Patent Application No. GB1717311.3 dated Apr. 20, 2018.

* cited by examiner

SLEEP ENHANCEMENT SYSTEM AND WEARABLE DEVICE FOR USE THEREWITH

CROSS REFERENCE TO RELATED APPLICATIONS

This is a U.S. National Phase Application under 35 U.S.C. § 371 of International Patent Application No. PCT/EP2018/078739, filed Oct. 19, 2018, which claims priority of United Kingdom Patent Application No. 1717311.3, filed Oct. 20, 2017. The entire contents of which are hereby incorporated by reference.

FIELD OF THE INVENTION

The invention relates to a system for detecting an electroencephalographic (EEG) response from a user in real time while the user is preparing for sleep, during sleep or waking from sleep. In particular, the invention relates to a system in which a detected EEG signal can be used to provide feedback, e.g. audio feedback and/or sensory symbiosis, that improves the user's sleep.

BACKGROUND

Wearable technology for monitoring physiological properties of a user during an activity is a recent and popular phenomenon. Wearable sensors may be self-contained, or may interface with other accessories, such as smartphones, smartwatches, tablet computers or the like. Collected information may be used to monitor performance and influence training, etc.

More recently, there is an increased interest in monitoring sleep patterns, e.g. to identify sleep stages such as awake, light sleep, deep sleep, rapid eye movement (REM) sleep, its impact on memory consolidation, cognitive recall rates and/or other human performance factors etc. It is widely acknowledged that poor sleeping habits negatively impact on physical and mental well-being. For example, it is known that sleep restriction or deprivation can result in impaired cognitive performance and even reduced life expectancy.

Such devices are typically implemented commercially using a wearable unit such as a wristband in combination with a smartphone. Such devices operate to detect a user's movement (e.g. using an accelerometer or microphone), heart rate, skin temperature, etc., and use this information to inaccurately derive information indicative of behavior during sleep.

US 2015/0297109 discloses a wearable device which detects an electroencephalographic (EEG) response from a user while listening to a musical piece on a static database. The EEG response may be used to categorize and tag that musical piece according to the self-selected mood it instils in the user. In one example, musical pieces that the user indicates induce restful sleep can be tagged as been useful for inducing future sleep. As a sleep state is approached, the volume of the music may automatically be faded down.

SUMMARY

At its most general, the present invention provides a system in which a wearable device detects an electroencephalographic (EEG) response from a user during sleep-related activity, e.g. trying to fall asleep, being asleep or waking up, and outputs an audio signal that is tailored, based on the EEG response, to enhance the user's sleep experience. In particular, an audio, thermal and/or olfactory signal may be used to facilitate any one or more of (i) a smooth path into REM sleep, (ii) a reduced potential for sleep being disturbed, and (iii) exit from sleep at an optimum time. In some examples, the system can be used to customize the user's sleep experience to match expectations or available time.

According to one aspect of the invention, there is provided a system for enhancing a user's sleep experience, the system comprising: a wearable unit arranged to be worn around a user's head; a sensor array mounted in the wearable unit, the sensor array comprising a plurality of sensor elements for making electrically conductive contact with a user's scalp; a detector mounted in the wearable unit, the detector being arranged to detect voltage fluctuations at each of the plurality of sensor elements and generate an electroencephalographic (EEG) signal therefrom; an audio output module mounted in the headgear, the audio output module being arranged to output an audio signal to be heard by the user; and a processing unit arranged to: identify sleep-related parameters in the EEG signal; and adjust properties of the audio signal based on the identified sleep-related parameters. In use, the system operates to tailor properties of an audio signal output to the user based on a detected EEG response. The tailoring may occur in real time. For example, the processing unit may be arranged to receive the EEG signal as a real-time data stream. The processing unit may dynamically adjust the properties of the audio signal based on the EEG signal. The tailoring of the audio signal may comprise synchronizing one or more properties of the audio signal with the identified sleep-related parameters. This may be achieved by time stamping the sleep-related parameters so that the audio signal can be mapped or matched to fit or correlate with the sleep-related parameters. For example, the sleep-related parameters may exhibit one or more patterns to which it is desirable to synchronize properties of the audio signal.

The audio signal may comprise a dominant white and/or pink noise component. The audio signal may be of natural sounds such as ambient activity, breaking waves, animal calls, blowing wind or background human-made sounds such as crowd noise or traffic, or synthesized sounds. The type of audio signal (i.e. white and/or pink noise) may be selectable, e.g. by the user.

To tailor the audio signal, the processing unit may be arranged to adjust any one or more of the audio signal's properties, such as intensity, frequency, tone, volume and rhythm. As mentioned above, the identified sleep-related parameters may include one or more patterns, e.g. periodic waveforms in the EEG signal. The processing unit may be arranged to adjust properties of the audio signal to increase its correlation to (and influence of) these periodic waveforms.

The sleep-related parameters may be extracted from computer analysis of the EEG signal. The analysis may be automated, i.e. performed by the processing unit. For example, the processing unit may be arranged to identify sleep-related signature waveforms in slow wave activity (SWA) in the EEG signal. The sleep-related signature waveforms may be identified by shape matching with a target variation, e.g. a known shape or feature of the EEG signal.

The EEG signal may be filtered to remove unwanted artefacts before the analysis is performed. For example, the processing unit may comprise a filter module for filtering the EEG signal before the sleep-related parameters are identified. The filter module may be arranged to remove non-sleep-related artefacts from the EEG signal. The non-sleeprelated artefacts may be identified based on a library of artefact norms to which the processing unit has access. Advantageously, the processing unit may comprise a machine learning module operable to customize the library of artefacts norms based on individually detected artefacts for the user. The filter module may thus "tune" itself to any given user.

The EEG signal itself may be obtained in a normal way. The plurality of sensor elements may be located in positions that are suitable for yielding EEG signals that exhibit the sleep-related parameters. For example, the sensor array may include a first set of sensor elements for detecting activity in a frontal lobe area of the user, and a second set of sensor elements for detecting activity in a parietal lobe area. The first and second sets of sensors are located on the wearable unit to adopt suitable positions at the front and rear of the user's head respectively when the wearable unit is worn.

The wearable unit may comprise an accelerometer for detecting head movement. The detected head movement may be used both to determine a sleep quality metric based on head movements detected by the accelerometer, and as a further filter to remove features from the EEG signal that are related to non-relevant movements detected by the accelerometer. In practice there may be a pair of accelerometers disposed on opposite sides of the wearable device, i.e. to be located on different sides of the user's head when the wearable unit is worn.

The system may be arranged to store and/or stream the EEG signal, e.g. for later use. A suitable memory may be provided for this purpose, e.g. in the wearable unit or elsewhere. The processing unit may be arranged to aggregate the EEG signal stored on the memory and/or streamed throughout a user's sleep cycle, generate therefrom neurofeedback data for the user, and display the neurofeedback data to the user. The neurofeedback may be indicative of the duration, nature and quality of the user's sleep, e.g. NREM or REM sleep, dream states or similar, based on the stored EEG signal.

The processing unit may be provided on the wearable unit, or may be on a remote computing device (e.g. smartphone, tablet, laptop or the like). In the latter example, the wearable unit may comprise a transceiver for wirelessly transmitting the EEG signal to the remote device and for wirelessly receiving a feedback signal from the processing unit. The feedback signal may comprise the audio signal having had its properties adjusted based on the sleep-related parameters. Alternatively, the audio signal may be obtained from a different source, whereby the feedback signal may comprise a control signal for adjusting properties of the audio signal at the wearable unit. In one example, the wearable unit has a local audio store thereon. In another example, the wearable device may be in wireless communication with a remote audio source to receive the audio signal.

According to another aspect of the invention, there is provided a wearable device comprising: a flexible band to be worn around a user's head; a sensor array mounted to the flexible band, the sensor array comprising a plurality of sensor elements for making electrically conductive contact with a user's scalp; a detector mounted in the wearable unit, the detector being arranged to detect voltage fluctuations at each of the plurality of sensor elements caused by the user's electroencephalographic (EEG) activity and to generate an EEG signal therefrom; and an audio output module mounted in the headgear, the audio output module being arranged to output an audio signal to be heard by the user, wherein properties of the audio signal are adjustable based on sleep-related parameters identified in the EEG signal. The wearable device according to this aspect may be used with the system described above, and any features of that system may be incorporated into this aspect of the invention.

The flexible band may comprise a strip of fabric arranged to fit around the user's head. For example, the flexible band may resemble an eye mask or bandana. The flexible band may be made of soft material and/or may include cushioning for comfort.

The flexible band may include a frontal portion for lying over the user's forehead when worn. The sensor array may comprise a first set of sensor elements mounted on the frontal portion. Similarly, the flexible band may have a rear portion for lying over a parietal lobe of the user when worn. The sensor array may comprise a second set of sensor elements mounted on the rear portion. The frontal portion may include an internal eye covering for locating over the user's eyes when the flexible band is worn. In one example, the flexible band may comprise an eye mask that also offers symbiotic sensory stimulation. For example, a pocket (e.g. formed as a soft pouch made from silk, similar fabric to the rest of the mask or the like) is provided on an inside surface of the eye covering. The pocket may be arranged to receive an insert for delivering a sensory experience, e.g. through changes in temperature, smell or the like. In one example, the insert may be a self-heating element that can be pre-treated with one or more sleep inducing oils such as lavender. The EEG signal that is obtained when such an insert is activated may be tagged in order to associate the user's response to that sensory output. The sensory output from the insert may be controllable in a similar way to the audio signal, e.g. to augment its effect and optimize the user's experience.

The audio output module may comprise one or more micro-speakers mounted in the wearable unit. The micro-speakers may comprise microfiber portions fabricated in the flexible band to improve user comfort, optimize acoustic transfer and/or cancel external noise.

The detector may be mounted on a substrate (e.g. flexible printed circuit board) that conforms to the shape of the flexible band. The flexible band may include a conductive interconnection structure that provides an electrical connection between the sensor array and the detector. The conductive interconnection structure may comprise a conductive fabric and/or ink sandwiched between a pair of insulation layers. The conductive interconnection structure may in turn be encased within layers of fabric that form the flexible band.

Other aspects, options and advantageous features are set out in the detailed description below.

BRIEF DESCRIPTION OF THE DRAWINGS

Embodiments of the invention are discussed in detail with reference to the accompanying drawings, in which.

DETAILED DESCRIPTION OF THE DRAWINGS

The disclosure herein relates to a system that may be used to monitor, control and improve sleeping habits. The system may provide a wearable unit (e.g. a sleep mask) that tracks an individual's sleep patterns based on the electrical activity generated by their brain. This approach has the potential to empower individuals to understand their sleeping habits with a level of fidelity that is impossible to achieve with existing commercial devices. The data generated by the system can be applied to state-of-art machine learning analysis to provide a measure of a user's sleep quality on each night based on their own sleeping patterns. The system may be used to improve sleep by presenting "white" or "pink" noise at optimal moments of the sleep cycle. By promoting slow-wave sleep and providing auditory stimulation in synchrony with one's own brain activity, the device may facilitate natural memory consolidation and learning processes that take place during sleep.

Different stages of sleep are characterized by qualitatively distinct changes in neuronal firing and the electrical activity generated by these changes is manifested on the scalp. Since the first observation some 80 years earlier, a plethora of research has established that applying sensors on the scalp (electrodes) whilst a subject sleeps provides a highly reliable measure of their sleep state.

A typical night's sleep involves cycling through stages of REM (rapid eye movement) and NREM (non-rapid eye movement) sleep. REM sleep is the period associated with dreaming and characterized by low voltage and mixed frequency EEG signals. In this state, the sympathetic nervous system is in a period of high arousal, but there are few bodily movements, with muscles being paralyzed. In contrast, in NREM, the body is more active, but the brain produces slower and stable signals, with the frequency of the signals becoming lower as one transitions from light sleep (stages 1 and 2) through to deep sleep (also referred to as slow wave sleep). This slow wave activity appears to be particularly important in the consolidation of memory and learning and is the worst time to be awoken, in that it is likely to leave one feeling groggy and fatigued.

The present invention relates in general to a brainwave sensing system for improving a user's sleep experience. The system comprises a wearable unit (e.g. eye mask, head band, bandana or the like) that is mountable on a user's head during sleep. As explained in more detail below, the wearable unit comprises an array of sensors for detecting an electroencephalographic (EEG) response from the user. The EEG response is processed to detect one or more sleep-related parameters. The wearable unit is also arranged to communicate an audio signal to the user, e.g. via one or more speakers (e.g. micro-speakers) mounted therein. The audio signal and/or properties of the audio signal may be influenced, e.g. controlled as part of a feedback process, based on the detected sleep-related parameters. The processing of the EEG response may take place either on the wearable unit itself or at a remote user terminal (e.g. smartphone, tablet, laptop or the like) that may be in wireless communication with the wearable unit. Similarly, the audio signal may be generated and/or controlled locally at the wearable unit or at the remote user terminal, whereupon it may be streamed to the wearable unit in any known manner.

The oscillations being captured in the EEG response may reflect state-dependent synchronized activity relating to the ways information is processed and communicated across neuronal cortical networks. These distinct stages of sleep may be differentially sensitive to sounds. The brain continually registers and processes auditory information throughout the night, but whether the sound wakes us, makes us move or even shift between different sleep stages is dependent on the current sleep stage and the type of sound being processed.

Research investigating the relationship between sound, sleep and EEG has demonstrated the potential benefits of providing specific types of sounds at key points in the sleep cycle. The most studied effect is the presentation of "white noise". White noise comprises an equal distribution of noise from all the possible frequencies that can be heard by the human ear and works by creating a masking effect that drowns out other sounds (i.e. sudden changes in sound frequency) that might disrupt in the early stages of sleep. In contrast to white noise, in pink noise, lower sound frequencies have greater power (the sound here is equivalent to rustling of leaves in a tree, or the waves one might hear on the beach). A growing number of experiments are demonstrating that pink noise could be beneficial for improving deep sleep and that presentation during deep/slow wave sleep has a positive impact on one's memory and learning.

The present invention leverages this understanding to provide a device that may assist to maximize the period of time spent in slow wave sleep and facilitate the consolidation of cognitive information processing.

Thus, the audio signal provided by the wearable device may be a type of white and/or pink noise, whose properties may be tailored based on the detected sleep-related parameters to improve the user's sleep process, e.g. by any one of more of:

augmenting non-rapid eye movement (NREM) sleep induction;
stabilizing NREM sleep rhythms;
increasing REM sleep iterations;
exiting sleep efficiently and at the optimum time.

Properties of the audio signal may be dynamically adjusted based on the detected EEG response as sleep progresses. This enables the audio signal to adapt to changes in the user's state, and can reduce the chance of the user being woken or otherwise interrupted.

The system may also be arranged to process the user's EEG response during the sleep process to recognize and record REM sleep dream-states. This information may be used after the user wakes to provide an interpretation of EEG response associated with the nature of the dreams. In one example, the system may be arranged to create a visual and/or sonic expression of the emotional content of the dreams for communication to the user (e.g. via the remote user terminal) as they wake, e.g. to facilitate a smooth transition to a woken state.

Figure 1:
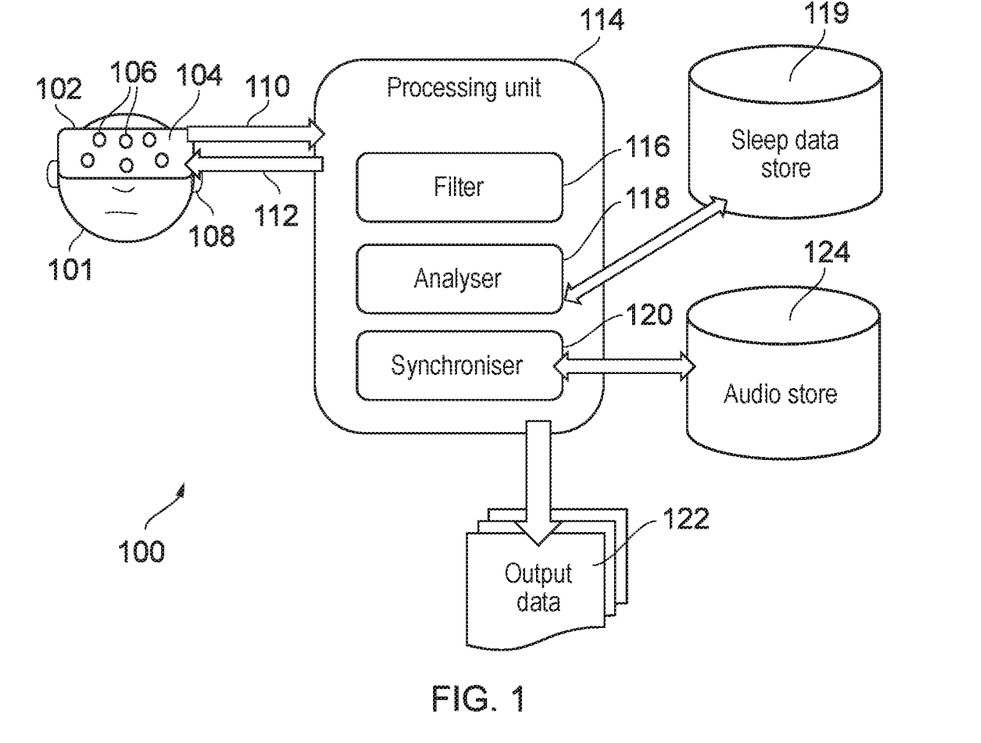
FIG. 1 is a schematic view of a biofeedback system that is an embodiment of the invention.

FIG. 1 is a schematic view of a biofeedback system 100 that is an embodiment of the invention. The system 100 comprises a wearable unit 102 that is worn on the head of a user 101. The wearable unit 102 preferably comprises a flexible strip 104 of material that passes around the user's head from front to back. The wearable unit 102 comprises an array of sensor elements 106 mounted or integrated into the strip 104. Each sensor element 106 is for obtaining an electroencephalographic (EEG) signal from a user when the wearable unit 102 is mounted on their head. Each sensor element 106 may be arranged to contact the user's scalp to obtain a suitable measurement. The sensor elements 106 may be located within the wearable unit 102 at suitable positions for obtaining an EEG signal from suitable nodes across the user's skull. The location of the sensor elements may be selected to facilitate detection of a set of sleep-related parameters. In one example, the sensor elements 106 may include a first set for location across the frontal lobe of the user 101, and a second set for location at the parietal lobe. Each set may have one or more sensor elements. The flexible strip 104 is shaped to include fabric portions that lie over the user's frontal and parietal lobes when the wearable unit is worn. The sensor elements 106 may be mounted on these fabric portions, e.g. as discussed in more detail below. In one example there are six sensors mounted over the frontal lobe at the front of the strip 104 when worn and two sensors over the parietal lobe at the rear of the strip 104 when worn. In one example, a first set of sensor elements may be located at or around the FP1, FP2, F3, F4, F7 and F8 positions, and a second set of sensor elements may be located at or around the O1 and O2 position when the flexible strip 104 is worn. The first set of sensor elements may each have a dry gel body for obtaining good contact on the skin over the frontal lobe. The second set of sensor elements may include a hair-penetrating structure to assist in obtaining a good contact with the scalp over the parietal lobe.

The wearable unit 102 may further comprise one or more audio output elements, e.g. a pair of speakers 108 mounted on the flexible strip to be at or over a user's ears when the first and second sets of sensor elements are correctly located. The speakers 108 may take any suitable form. They may be micro speakers that lie adjacent the user's ears. They may comprise earbuds for locating in the user's ears. In one example, the speakers 108 may comprise a deformable portion, e.g. made from microfiber, for ensuring comfortable contact with the user, optimum acoustic performance and/or external noise cancellation. The deformable portion may be integrated formed with the flexible strip 104.

Figure 2:
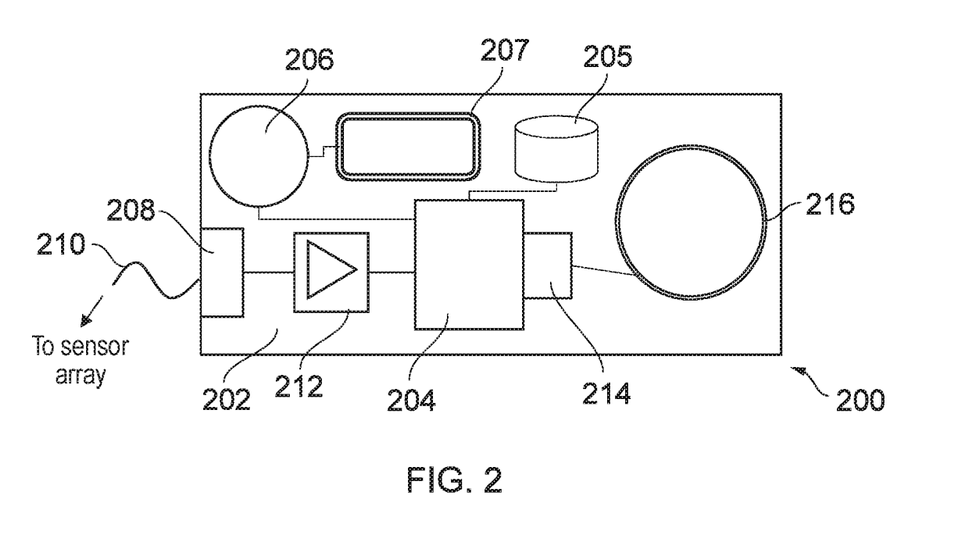
FIG. 2 is a schematic view of a portable processing unit for mounting in a wearable article for use in an embodiment of the invention.

The wearable unit 102 includes a local processing unit (an example of which is shown in FIG. 2), for controlling the sensor array and generating (then amplifying) an EEG signal based on readings from the sensor array. The wearable unit 102 may be equipped with a wireless transmitter for transmitting the EEG signal 110 to a processing unit 114 for further processing. The wireless transmitter may send the signal over any suitable network using any suitable protocol, e.g. WiFi, Bluetooth®, etc. The wireless transmitter may include 4G or 5G connectivity for immediate transmission and real-time response.

Additionally or alternatively, the wearable unit 102 may include a storage unit, e.g. a computer writable memory such as flash memory or the like, where information can be stored in the wearable unit and then downloaded later (e.g. via a wireless or wired link).

The processing unit 114 is a computing device used to analyze the EEG signal and generate or control an audio signal to be output by the speakers 108. The processing unit 114 may be arranged to transmit a feedback signal 112 (e.g. a control signal or an audio stream) back to the wearable unit 102.

Any computing device capable of communicating with the wearable unit may be used as the processing unit 114. For example, the processing unit 114 may be a smartphone, tablet computer, laptop computer, desktop computer, server computer or the like. The processing unit 114 comprises a memory and a processor for executing software instructions to perform various functions using the EEG signal. In the example illustrated in FIG. 1, the processing unit 114 is shown to have three modules that perform different functions.

The processing unit 114 comprises a filter module 116 arranged to clean up the received EEG signal, e.g. by filtering out environmental artefacts and/or other unwanted frequencies, e.g. associated with unrelated brain activity such as blinking, chewing, moving, tasting, etc. The filter module 116 may operate using algorithms arranged to recognize artefact waveforms, e.g. based on input from a normative databases, in the received EEG signal. The algorithms may be adapted to learn the user's specific waveform for each type of artefact, and update the recognition routine accordingly. The filtering process may thus become quicker and more adept with increased use. The wearable unit 102 may comprise a movement sensor (e.g. a pair of accelerometers mounted on either side of the headband). The movement sensor may monitor changes in head position associated with the quality of sleep and provide a reference point to assist in removing irrelevant data caused by other types of movement.

In one example, the filter module may be arranged to extract data corresponding to target EEG frequency bands from the obtained EEG signal.

The central processing unit 106 comprises an analyzer module 118 that is arranged to process the EEG signal (e.g. after filtering by the filter module 116) to yield information indicative of the user's mental state, and in particular to obtain information relating to one or more sleep-related parameters. The analyzer module 118 may be configured to process the (filtered) EEG signal in a manner such that the sleep-related information is effectively generated in real time.

The initial EEG signal obtained using readings from the sensor elements 106 may comprise one or more EEG data maps that represent the variation over time of a brainwave electrical signal detected at each sensor location. The EEG data maps may be processed to generate responses from each sensor in a plurality of EEG frequency bands (e.g. Alpha, Beta, Theta, etc.). Each sensor may be arranged to capture up to six brainwave frequencies.

The analyzer module 118 operates on the filtered EEG signal to identify sleep-related parameters, or other relevant parameters, such as those influences by other sensory stimulation that may be applied (e.g. heat, smell, or the like). In one example, the sleep-related parameters are based on K-complex and similar slow moving waves, which are typically evidenced by EEG slow wave activity (SWA) across the frontal lobe, and specifically in non-lemniscal ascending pathways to the thalamo-cortical system. In particular, the sleep-related parameters identified by the analyzer module 118 may include:

sleep "spindles", which derive from a thalamo-cortical rhythm that manifests in EEG as a brief 11-15 Hz oscillation across the frontal lobe; and unique (but recurring) grades of peak and trough in slower moving waves (e.g. in the Delta band of 0.5 to 4 Hz) across the parietal lobe, which are evidence of emotion in REM sleep dream-states.

The analyzer module 118 is arranged to produce an output data stream in which the sleep-related parameters are identified and time-stamped. The output data stream is delivered to a synchronizer module 120 effectively as real-time data indicative of a user's current sleep state.

The synchronizer module 120 may comprise viral machine learning software that is arranged to synchronize the output data stream with time-stamped audio data (e.g. white noise, pink noise or white/pink noise dominated sound) from an audio store 124. Although the synchronizer module is shown in the processing unit 114 in this example, it may be located elsewhere, e.g. on the wearable unit 102 or in a cloud-based server that is in communication with the processing unit 114. Similarly, the audio store 124 may be in the same location as the synchronizer module 120 or may be located elsewhere. The audio store 124 may be any suitable data storage for audio data. The audio data may be loaded into a database in a memory on the wearable unit 102 or in the processing unit 114. The audio store 124 may be updatable, e.g. to provide new audio tracks or the like.

The time-stamped audio data is supplied to the wearable unit 102, e.g. as part of feedback signal 112, to be played through the speakers 108. The initial type of audio data may be selectable by the user, e.g. through a suitable user interface on the wearable device 102 or processing unit 114. The user may select the initial audio in advance of going to sleep. For example, the processing unit 114 may have an app running thereon through which the user can interact with the system. The data used by the app may be stored locally on the device or may be downloaded/streamed from a server. Exemplary types of white and/or pink noise dominated audio may include ambient activity, breaking waves, animal calls, blowing wind, background human-made sounds, crowd noise, traffic noise, or synthesized sounds etc. It may be possible for a user to record their own preferred type of white/pink noise for use in the system.

The synchronizer module 120 is arranged to manipulate or enhance the audio data, e.g. the user's initial choice of white noise, based on the output data stream. The enhancement may occur at the processing unit 114, whereby the feedback signal 112 conveys the enhancement audio signal. Alternatively or additionally, the enhancement may occur at the wearable unit 102, whereby the feedback signal 112 conveys a control signal (together with or separately from the audio signal) that can be used by the wearable unit 102 to manipulate the audio that is output from the speakers.

The manipulation or enhancement of the audio signal may be performed by adjusting any of the audio signal's properties—such as intensity, frequency, tone, volume, rhythm and correlation to waveforms identified in the data stream. To prevent aural fatigue, a different type of white and/or pink noise audio may be automatically introduced if needed.

One aim of the manipulation may be to enhance the observed K-complex and slow moving waves in the EEG signal. By evoking larger amplitude, steeper slope SWA involving broader cortical regions than most spontaneous SWA, it is possible to accelerate entry into NREM sleep, increase the duration of REM sleep, optimize rhythms in both NREM and REM sleep, and increase release of sleep "spindles", which in turn can stabilize depth of sleep and reduces the impact of unwanted external stimuli waking the user up. The user's response to the enhanced audio signal can be detected in the subsequently detected EEG signal. It is therefore possible to effectively set up a feedback loop where the manipulation of the audio is tuned to move towards a desired EEG response.

The ability of the synchronizer to dynamically respond to the detected EEG response may be particular advantageous because the K-complex and slow moving waves are homeostatically regulated, and therefore their form can vary depending on a user's activity. For example, the longer a user has been awake, the more frequent and larger their SWA will be during subsequent sleep. The synchronizer module 112 can "tune in" to these variations and adapt the audio accordingly. Moreover, the processing unit 114 (e.g. the synchronizer module or analyzer module) may be arranged to compare a detected real time SWA with an average SWA recorded for a user to provide a real-time index of that user's sleep need. This information can also be used to determine how to adapt or enhance the audio signal.

The functionality of the processing unit 114 discussed above concerned its ability to improve a user's sleep experience in real time by enhancing an audio signal and correlating the efficacy of symbiotic sensory influences. However, the processing unit 114 may also be arranged to record, aggregate and a perform post-event analysis on the EEG signals collected throughout a user's sleep cycle to deliver automated neurofeedback to the user when they wake. For example, the neurofeedback may be provided via an app on a user terminal (e.g. smartphone or tablet) every morning.

In one example, the sleep-related information from the analyzer module 114 may be transmitted to a sleep data store 119 (e.g. a memory). The sleep-related information may be aggregated or otherwise processed to provide a summary of the user's sleep process for a given night's sleep. The summary may be displayed on the processing unit 114 or otherwise communicated e.g. as output data 122. For example, where the processing unit 114 is embodied as a smartphone, the output data 122 may be used (e.g. by an app running on the smartphone) to generate a graphical display to be shown on the screen of the smartphone. In other arrangements, the data may be transmitted to another device for storage or display.

The output data 122 may be used by the app in a number of ways. For example, the app may inform a user of their current sleep balance, e.g. as a credit or debt. The app may indicate benefits or risks associated with the sleep balance, or may offer bespoke wellbeing or lifestyle advice and products. For example, the app may suggest or provide alternative types of white and/or pink noise or different types of symbiotic sensory products that are better suited to the user's observed sleep pattern. In one example, the app may generate an emotional 'storyboard' of REM dreams recorded, to provide a multimedia feedback on the user's sleep experience.

The overall aim of the system is to provide the user with a well-regulated, efficient and optimized sleep pattern. Physical repetition of sleep patterns coupled with increased neuroplasticity during SWA can improve the speed at which a user goes to sleep, the quality of that sleep, as well as the user's memory consolidation. Moreover, it may be possible for a user to select in advance a desired sleep pattern to yield a certain outcome, e.g. quickest refreshment, longest duration, vividest dreams, mitigation of normally disruptive factors e.g. alcohol, jet lag etc.

The output data may be shared by the user, e.g. with their social circle via social media or with other entities for research or commercial purposes, such as retail/lifestyle informatics, or the like.

The functions of the processing unit 114 may be all performed on a single device or may be distributed among a plurality of devices. For example, the filter module 116 may be performed on the wearable unit 102, or a smartphone communicably connected to the wearable unit 102 over a first network. The analyzer module 118 may be provided on a separate server computer (e.g. a cloud-based processor)

that is communicably connected to the processing unit 114 over a second network (which may be a wired network).

FIG. 2 is a schematic view of a portable processing unit 200 that can be used in a wearable unit that is an embodiment of the invention. The processing unit 200 comprises a flexible substrate 202 on which components are mounted. The flexible substrate 202 may be mounted, e.g. affixed or otherwise secured, to the flexible strip of the wearable unit.

On the substrate 202 there is a processor 204 that control operation of the unit, and a battery 206 for powering the unit. The substrate 202 includes an electrode connection port 208 from which a plurality of connector elements 210 extend to connect each sensor element (not shown) to the processing unit 200. The wearable sensor operates to detect voltage fluctuations at the sensor element locations. The processing unit 200 includes an amplification module 212 (e.g. a differential amplifier or the like) for amplifying the voltages seen at the sensors. The amplification module 212 may be shielded to minimize interference.

The processing unit 200 may be configured to take reading from multiple sensors in the array at the same time, e.g. by multiplexing between several channels. In one example, the device may have eight channels, but the invention need not be limited to this number. The voltage fluctuations may be converted to a digital signal by a suitable analog-to-digital converter (ADC) in the processing unit. In one example, a 24-bit ADC is used, although the invention need not be limited to this. The processor 204 may be configured to adjust the number of channels that are used at any given time, e.g. to enable the ADC sampling rate on one or more of the channels to be increased or to switch off channels that have an unusable or invalid output. The ADC sampling rate for eight channels may be 512 Hz, but other frequencies may be used.

The digital signal generated by the processing unit is the EEG signal discussed above. The processing unit 200 includes a transmitter module 214 and antenna 216 for transmitting the EEG signal to the processing unit 114. The transmitter module 214 may be any suitable short to medium range transmitter capable of operating over a local network (e.g. a picocell or microcell). In one example, the transmitter module 214 comprises multi-band (802.11a/b/g/n) and fast spectrum WiFi with Bluetooth® 4.2 connectivity.

The battery 206 may be a lithium ion battery or similar, which can provide a lifetime of up to 24 hours for the device. The battery may be rechargeable, e.g. via a port (not shown) mounted on the substrate 202, or wireless via an induction loop 207.

The processing unit 200 may include a storage device 205 communicably connected to the processor 204. The storage device 205 may be a computer memory, e.g. flash memory or the like, capable of storing the EEG signal or any other data needed by the processing unit 200.

The processing unit 200 may be mounted within the fabric of the headwear within which the wearable sensor is mounted. The electrical connection between the sensor elements and the substrate may be via wires, or, advantageously, may be via a flexible conductive fabric or ink. The conductive fabric or ink may be multi-layered, e.g. by having a conductive layer sandwiched between a pair of shield layers. The shield layers may minimize interference. The shield layers may be waterproof or there may further layers to provide waterproofing for the connections. With this arrangement, the wearable sensor can be mounted in a comfortable manner without sacrificing signal security or integrity.

Figure 3:
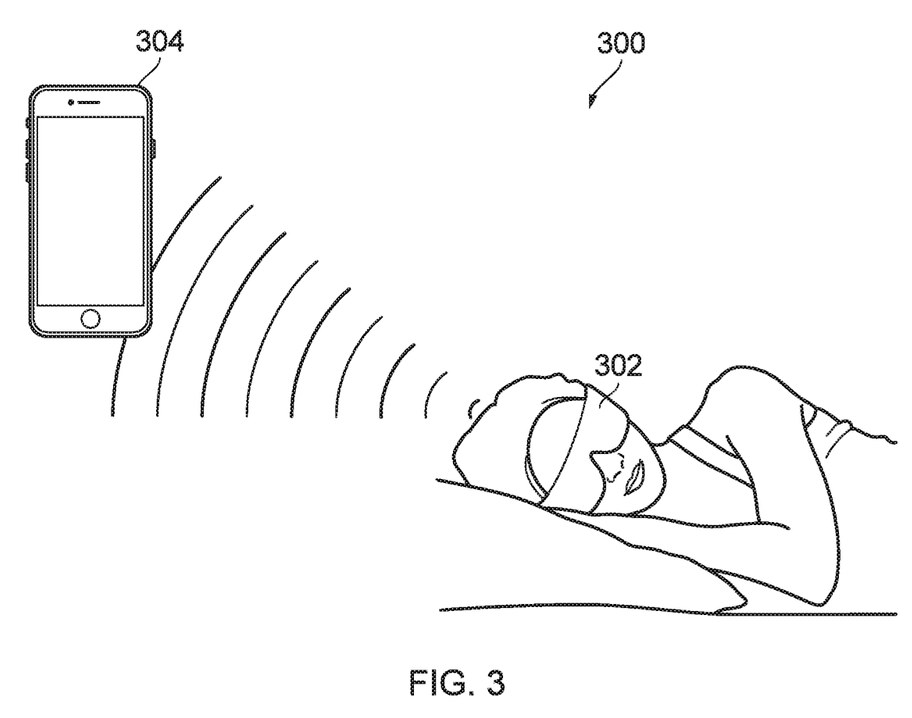
FIG. 3 is a schematic view of a system according to the invention in use.

FIG. 3 is a schematic view of a biofeedback system 300 that is an embodiment of the invention. In this example, the system 300 comprises an eye mask 302 that corresponds to the wearable unit discussed above. The eye mask 302 is in two-way wireless communication with a smartphone 304. The eye mask 302 transmits a detected EEG signal to the smartphone 304, which performs the functions of the processor unit discussed above and returns a feedback signal, whereupon the eye mask 302 plays back audio for the user that has been enhanced using the detected EEG signal. The smartphone 304 runs an app through which the user can interact with the system, e.g. by selecting a type of audio to begin, reviewing output data collected from a previous night's sleep and/or augmenting the next sleep pattern.

Figure 4A:
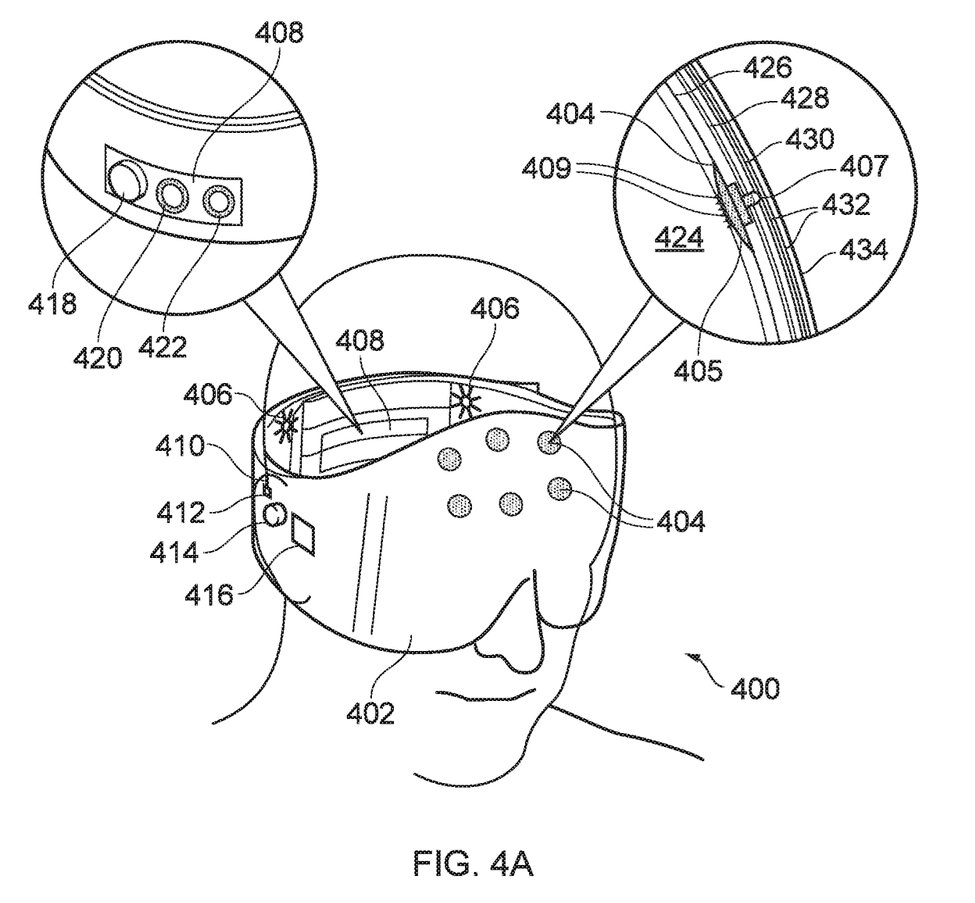
FIG. 4A is a front right perspective view of an eye mask incorporating an electroencephalographic (EEG) sensing and audio feedback unit that is an embodiment of the invention.

FIG. 4A is a front right perspective view of an eye mask 400 incorporating an electroencephalographic (EEG) sensing and audio feedback unit that is an embodiment of the invention. The eye mask 400 is an example of the wearable unit discussed above.

The eye mask 400 comprises a flexible strip 402, e.g. of soft fabric or the like, that can fit around a user's head and conform to their face. The flexible strip 402 includes a forward portion for covering the user's eyes. The flexible strip 402 may be an elasticated band or may include one or more elasticated regions to allow the strip to resiliently deform to fit around the user's head. Alternatively, as shown in FIG. 4A, the flexible strip 402 may be an elongate piece having one or more fasteners that enable the strip to be wrapped around a user's head and secured in place. The one or more fasteners may include hook and loop fastenings or the like.

The flexible strip 402 includes a frontal portion that extends above the eye-covering forward portion to lie over the user's forehead when worn. An array of six sensor elements 404 are disposed in the frontal portion. At the rear of the flexible strip 402 a processing unit 408 (such as that discussed with respect to FIG. 2 above) is provided, e.g. on a flexible printed circuit board. A second array of two sensor elements 406 is also provided at the rear of the flexible strip 402. In this example, the sensor elements 406 are located on opposite sides of the processing unit 408 in a position where they will contact a region of scalp adjacent the parietal lobe.

As shown in a first magnified inset of FIG. 4A, the processing unit 408 has a battery 418, wireless charging coil 420 and transmitter 422 mounted thereon. These components may be protected ergonomically and/or electrically shielded from the user's scalp by an additional cushion pad formed on the inner surface of the flexible strip, if necessary.

The array of sensor elements 404 are connected to the processing unit 408 via interconnections that are fabricated within the flexible strip 402 itself. As shown in a second magnified cross-sectional inset of FIG. 4A, this is achieved by forming the flexible strip as a multi-layered structure in which a signal carrying layer 430 is sandwiched between a pair of insulating layers 432, which in turn are between an inner protective layer 426 and an outer protective layer 434. The inner protective layer 426 may be a fabric layer that is in contact with a user's head. On top of the inner protective layer 426 is a layer of foam 428 that protects the user's scalp from unwanted and potentially uncomfortable contact with the conductive layer and processing unit. The signal carrying layer 430 may be formed from a conductive fabric or ink, e.g. a flexible electrically conductive material that electrically connects the sensor elements to the processing unit. The inner and outer insulation layers 432 shield the conductive fabric, e.g. to minimize interference with the signals carried by it. The outer protective layer 434 may be a fabric layer, e.g. formed of any conventional material used for eye masks.

Each sensor element 404 is mounted on the inner fabric layer 426 such that it contacts the user's forehead when the eye mask 400 is worn. Each sensor element 404 comprises a soft deformable body 405 (e.g. formed from dry silicone gel or the like) on which a plurality of conductive micro-pins 409 project to make intimate contact with the user's skin in order to obtain a good signal via the user's skull 424. A micro-electrode 407 is mounted centrally in the body 405. The micro-electrode 407 is in electrical contact with the micro-pins 409 at one end and extends though the inner fabric layer 426, foam layer 428 and inner insulation layer 432 to contact the conductive fabric layer 430 at another end.

A reference electrode 412 is mounted elsewhere on the eye mask 400 to supply a reference voltage against which the voltage fluctuations are measured. In this example, the reference electrode comprises a graphite pad connected to the processing unit 408 by a fiberglass wire 410.

A micro-speaker 414 is mounted on the flexible strip 402 in a side region that lies over or adjacent one of the user's ears when the eye mask is worn. There may be another micro-speaker on the opposite side of the flexible strip. The micro-speaker 414 is in communication with the processing unit 408 to output audio to the user as explained above. The micro-speaker 414 may be connected by suitable cables, conductive fabrics and/or inks (not shown) that pass within the layers of the flexible strip.

An accelerometer 416 is also mounted on the flexible strip 402 in a side region. There may be another accelerometer on the opposite side of the flexible strip. The accelerometer 416 is in communication with the processing unit 408 to provide information about movement and/or orientation of the user's head. This information can be used in part of the filtering process performed on the EEG signal from the sensors as discussed above.

Figure 4B:
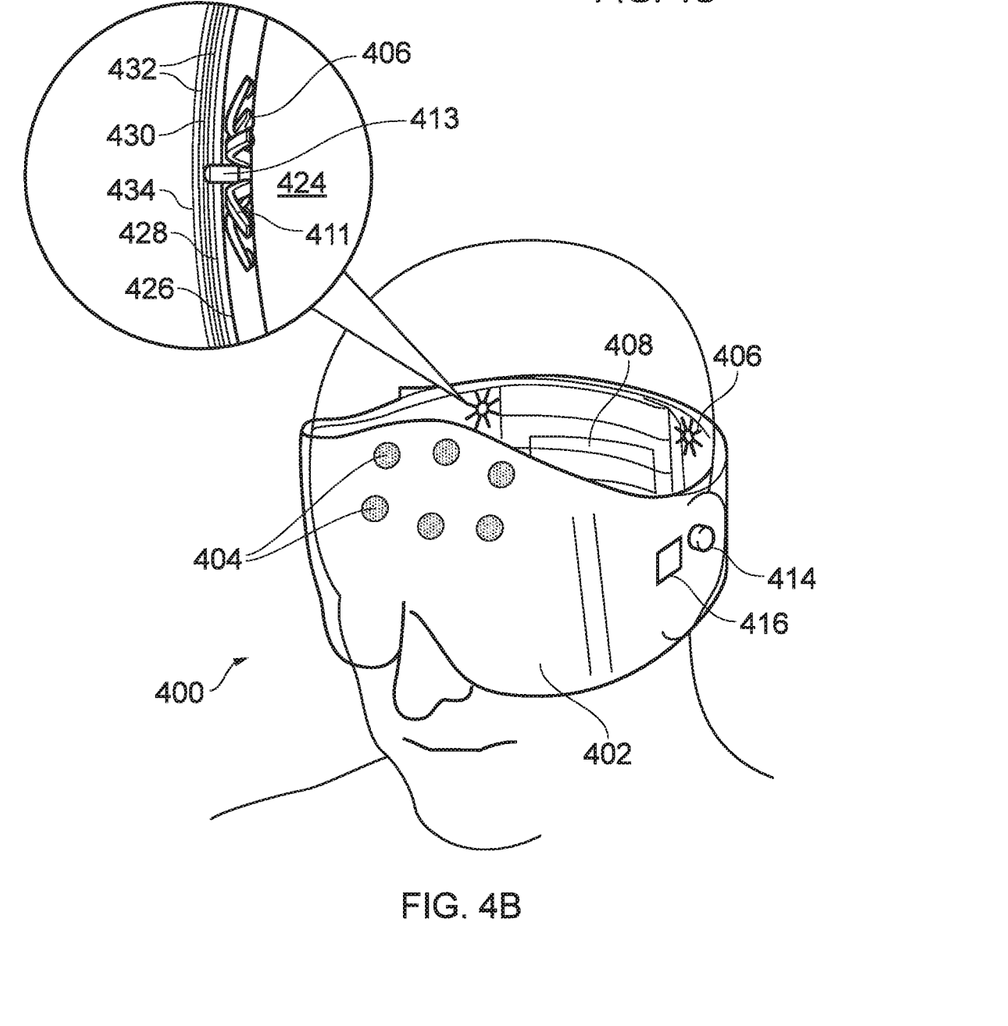
FIG. 4B is a front left perspective view of the eye mask shown in FIG. 4A.

FIG. 4B is a front left perspective view of the eye mask 400 shown in FIG. 4A. Features in common with FIG. 4A are given the same reference number and are not described again. The view in FIG. 4B shows the micro-speaker 414 and accelerometer 416 disposed on the other side of the flexible strip 402.

The magnified cross-section inset of FIG. 4B shows the how the sensor elements 406 at the rear of the flexible strip 402 engage with the user's skull 424. Similarly to the sensor elements 404 in the frontal region, the rear sensor elements 408 are connected to the processing unit 408 via the signal carrying layer 430 within the multi-layered structure of the flexible strip 402. In this example, each rear sensor element 406 provides a dry electrode connection to the user's scalp, i.e. the device does not need to be used with a conductive gel or the like. The sensor element 406 comprises a resiliently flexible star-shaped body 411, which may be made from any suitable material, e.g. conductive plastic, graphite, or the like.

Figure 4C:
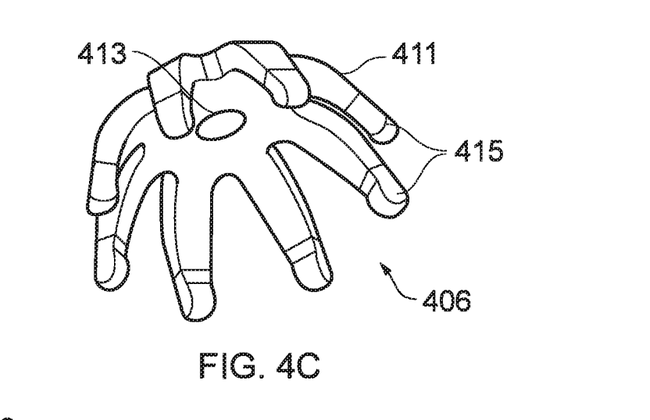
FIG. 4C is a magnified view of a hair penetrating sensor element that can be used with the eye mask shown in FIG. 4A.

The star-shaped body 411 comprises a plurality of legs extending radially outwardly from a central portion. The body 411 operates as a hair-penetrating member. The legs flex outwards as the central portion is pushed onto a surface (e.g. the user's scalp). The end of each leg acts to push aside hair on the scalp to ensure a good physical contact. The legs may have a rubberized tip 415 or the like to improve grip and stability. A conductive micro-electrode 413, e.g. made from gold or similar, is mounted at the central portion of the body to contact the user's scalp when the sensor element is pushed against it. In FIG. 4B the sensor element 406 is shown in contact with a user's scalp. The tension in the legs acts to retain the central portion in contact with the scalp. FIG. 4C shows the sensor element 406 when the body 411 is not pressed against the user's scalp.

Figure 5A:
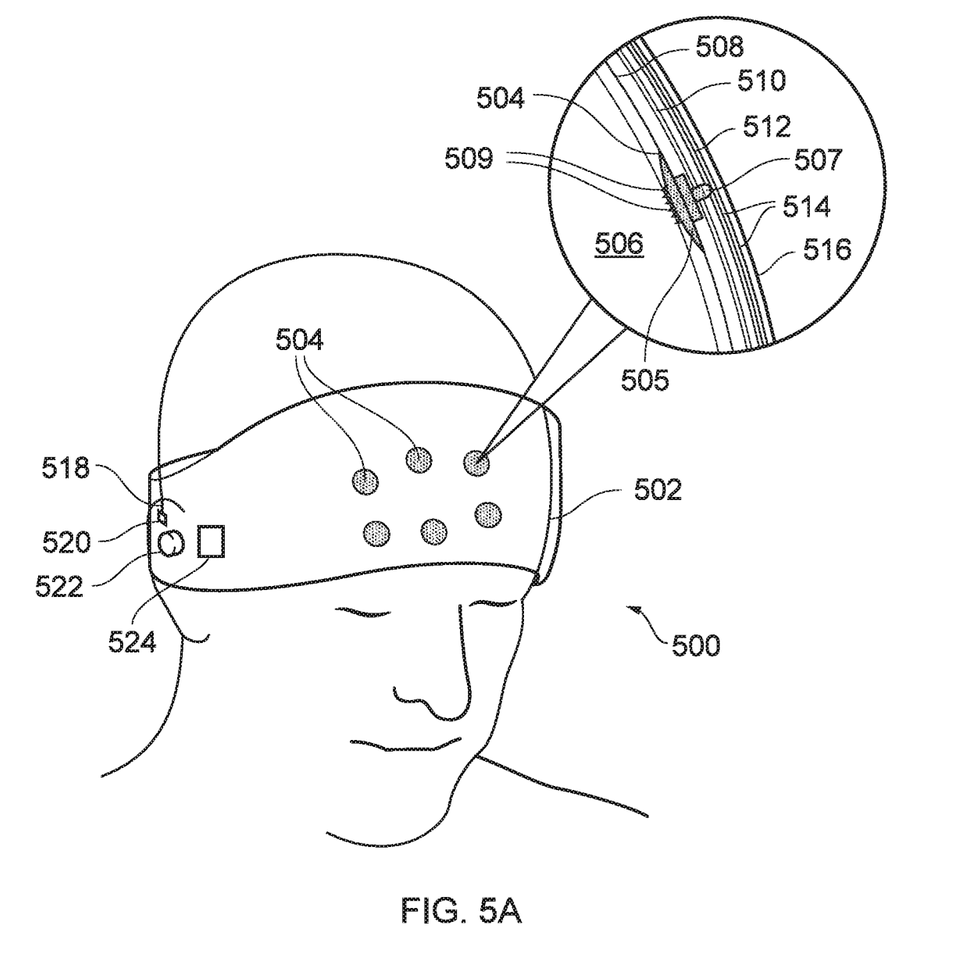
FIG. 5A is a front perspective view of a flexible head band incorporating an electroencephalographic (EEG) sensing and audio feedback unit that is another embodiment of the invention.

FIG. 5A is a front right perspective view of a head band 500 incorporating an electroencephalographic (EEG) sensing and audio feedback unit that is an embodiment of the invention. The head band 500 is an example of the wearable unit discussed above.

The eye mask 500 comprises a flexible strip 502, e.g. of soft fabric or the like, that can fit around a user's head and conform to their face. The flexible strip 502 may take the form of a bandana or the like. For example, the flexible strip 502 may be an elasticated band or may include one or more elasticated regions to allow the strip to resiliently deform to fit around the user's head. Alternatively, as shown more clearly in FIG. 5B, the flexible strip 502 may be an elongate piece having one or more fasteners on opposite ends thereof. The strip may be wrapped around a user's head so that the opposite ends can overlap and be secured to one another to hold the head band in place. The one or more fasteners may include hook and loop fastenings or the like.

Unlike the eye mask described above, the head band 500 may lie above the user's eyes, e.g. over their forehead. The flexible strip 502 includes a frontal portion that lies over the user's forehead when worn. An array of six sensor elements 504 are disposed in the frontal portion.

The array of sensor elements 504 are connected to a processing unit 408 (shown in FIG. 5B) via interconnections that are fabricated within the flexible strip 502 itself. As shown in a magnified cross-sectional inset of FIG. 5A, this is achieved by forming the flexible strip as a multi-layered structure in which a signal carrying layer 512 is sandwiched between a pair of insulating layers 514, which in turn are between an inner protective layer 508 and an outer protective layer 516. The inner protective layer 508 may be a fabric layer that is in contact with a user's head. On top of the inner protective layer 508 is a layer of foam 510 that protects the user's scalp from unwanted and potentially uncomfortable contact with (and/or electrically undesirable interference from) the conductive layer and processing unit. The signal carrying layer 512 may be formed from a conductive fabric and/or ink, e.g. a flexible electrically conductive material that electrically connects the sensor elements to the processing unit. The inner and outer insulation layers 514 shield the conductive fabric, e.g. to minimize interference with the signals carried by it. The outer protective layer 516 may be a fabric layer.

Each sensor element 504 is mounted on the inner fabric layer 508 such that it contacts the user's forehead when the head band 500 is worn. Each sensor element 504 comprises a soft deformable body 505 (e.g. formed from dry silicone gel or the like) on which a plurality of conductive micro-pins 509 project to make intimate contact with the user's skin in order to obtain a good signal via the user's skull 506. A micro-electrode 507 (e.g. formed from gold or the like) is mounted centrally in the body 505. The micro-electrode 507 is in electrical contact with the micro-pins 509 at one end and extends though the inner fabric layer 508, foam layer 510 and inner insulation layer 514 to contact the conductive fabric layer 512 at another end.

A reference electrode 520 is mounted elsewhere on the head band to supply a reference voltage against which voltage fluctuations are measured. In this example, the reference electrode 520 comprises a graphite pad connected to the processing unit 526 by a fiberglass wire 518.

A micro-speaker 522 is mounted on the flexible strip 502 in a side region that lies over or adjacent one of the user's ears when the eye mask is worn. There may be another micro-speaker on the opposite side of the flexible strip. The micro-speaker 522 is in communication with the processing unit 526 to output audio to the user as explained above. The micro-speaker 522 may be connected by suitable cables (not shown) that pass within the layers of the flexible strip.

An accelerometer 524 is also mounted on the flexible strip 502 in a side region. There may be another accelerometer on the opposite side of the flexible strip. The accelerometer 524 is in communication with the processing unit 526 to provide information about movement and/or orientation of the user's head. This information can be used in part of the filtering process performed on the EEG signal from the sensors as discussed above.

Figure 5B:
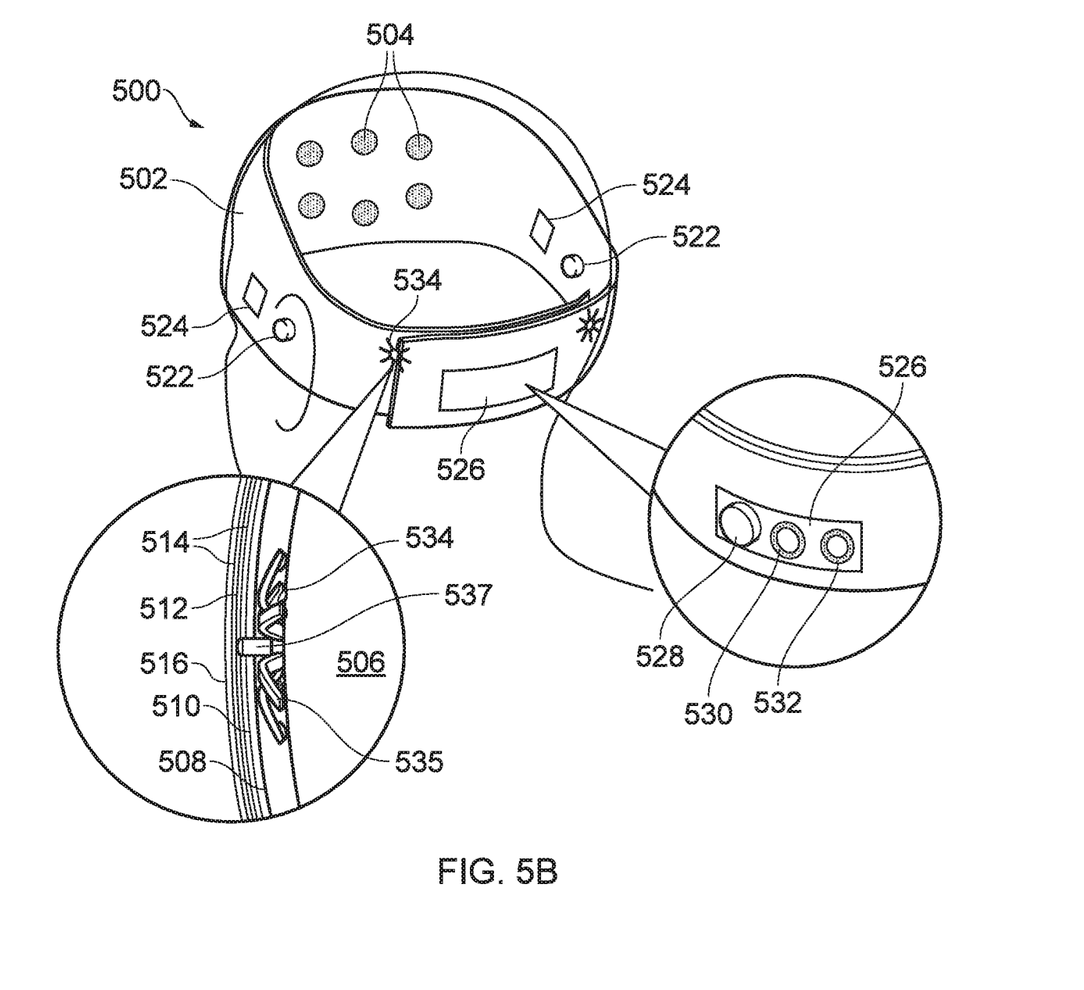
FIG. 5B is a rear perspective view of the flexible head band shown in FIG. 5A.

FIG. 5B shows a rear perspective view of the head band 500. Features in common with FIG. 4A are given the same reference number and are not described again. At the rear of the flexible strip 502 a processing unit 526 (such as that discussed with respect to FIG. 2 above) is provided, e.g. on a flexible printed circuit board. A second array of two sensor elements 534 is also provided at the rear of the flexible strip 502. In this example, the sensor elements 534 are located on opposite sides of the processing unit 526 in a position where they will contact a region of scalp adjacent the parietal lobe.

As shown in a first magnified inset of FIG. 5B, the processing unit 526 has a battery 528, wireless charging coil 530 and transmitter 532 mounted thereon. These components may be protected ergonomically and/or electrically shielded from the user's scalp by an additional cushion pad formed on the inner surface of the flexible strip, if necessary.

The view in FIG. 5B shows that there are micro-speakers 522 and accelerometers 524 disposed on both sides of the flexible strip 502.

A second magnified cross-section inset of FIG. 5B shows the how the sensor elements 534 at the rear of the flexible strip 502 engage with the user's skull 506. Similarly to the sensor elements 504 in the frontal region, the rear sensor elements 534 are connected to the processing unit 526 via the signal carrying layer 512 within the multi-layered structure of the flexible strip 502. In this example, each rear sensor element 534 provides a dry electrode connection to the user's scalp, i.e. the device does not need to be used with a conductive gel or the like. The sensor element 534 comprises a resiliently flexible star-shaped body 535, which may be made from any suitable material, e.g. conductive plastic, graphite, or the like.

The star-shaped body 535 comprises a plurality of legs extending radially outwardly from a central portion. The body 535 operates as a hair-penetrating member. The legs flex outwards as the central portion is pushed onto a surface (e.g. the user's scalp). The end of each leg acts to push aside hair on the scalp to ensure a good physical contact. The legs may have a rubberized tip or the like to improve grip and stability. A conductive micro-electrode 537, e.g. made from gold or similar, is mounted at the central portion of the body to contact the user's scalp when the sensor element is pushed against it. In FIG. 5B the sensor element 534 is shown in contact with a user's scalp. The tension in the legs acts to retain the central portion in contact with the scalp.

The invention claimed is:

1. A system for enhancing a sleep experience of a user, the system comprising:
a wearable unit arranged to be worn around a head of the user;
a sensor array mounted in the wearable unit, the sensor array comprising a plurality of sensor elements for making electrically conductive contact with a scalp of the user;
a detector mounted in the wearable unit, the detector being arranged to detect voltage fluctuations at each of the plurality of sensor elements and generate an electroencephalographic (EEG) signal therefrom;
an audio output module mounted in the wearable unit, the audio output module being arranged to output an audio signal to be heard by the user; and
a processing unit arranged to:
identify sleep-related parameters in the EEG signal; and
adjust one or more properties of the audio signal based on the identified sleep-related parameters,
wherein the processing unit comprises a filter module for filtering the EEG signal before the sleep-related parameters are identified, wherein the filter module is arranged to:
identify non-sleep-related artifacts based on a library of artifacts norms; and
remove the non-sleep-related artifacts from the EEG signal,
wherein the wearable unit comprises a pair of opposed accelerometers for detecting head movement,
wherein the filter module is arranged to filter the EEG signal, based on data from the pair of accelerometers, to remove irrelevant signals related to head movement, and
wherein the processing unit is arranged to determine a sleep quality metric based on relevant head movements detected by the pair of accelerometers.

2. The system of claim 1, wherein the processing unit is arranged to receive the EEG signal as a real-time data stream, and wherein the processing unit is arranged to:
dynamically adjust the one or more properties of the audio signal based on the EEG signal; and
synchronize the one or more properties of the audio signal with the identified sleep-related parameters.

3. The system of claim 1, wherein the audio signal comprises a dominant white or pink noise component.

4. The system of claim 1, wherein the one or more properties of the audio signal include any of intensity, frequency, tone, volume and rhythm.

5. The system of claim 1, wherein the identified sleep-related parameters include periodic waveforms in the EEG signal, and wherein the processing unit is arranged to adjust the one or more properties of the audio signal to increase a correlation of the audio signal to the periodic waveforms.

6. The system of claim 1, wherein the processing unit is arranged to analyze the EEG signal to identify sleep-related signature waveforms by shape matching with a target variation.

7. The system of claim 1, wherein the processing unit comprises a machine learning module operable to update the library of artifacts norms based on detected artifacts for the user.

8. The system of claim 1 comprising a memory for storing the EEG signal, wherein the processing unit is arranged to:
aggregate the EEG signal, wherein the EEG signal is stored on the memory throughout a sleep cycle of a user,
generate therefrom neurofeedback data for the user, and
display the neurofeedback data to the user.

9. The system of claim 1, wherein the processing unit is on a remote device, and wherein the wearable unit comprises a transceiver for wirelessly transmitting the EEG signal to the remote device and for wirelessly receiving a feedback signal from the processing unit.

10. The system of claim 9, wherein the feedback signal comprises the audio signal having the one or more properties that have been adjusted based on the sleep-related parameters, or a control signal for adjusting the one or more properties of the audio signal at the wearable unit.

11. The system of claim 1, wherein the wearable unit is wirelessly communicable with a remote audio source to receive the audio signal.

12. A wearable device comprising:
a flexible band to be worn around a head of a user;
a sensor array mounted to the flexible band, the sensor array comprising a plurality of sensor elements for making electrically conductive contact with a scalp of a user;
a detector arranged to detect voltage fluctuations at each of the plurality of sensor elements caused by electro-encephalographic (EEG) activity of the user and to generate an EEG signal therefrom; and
an audio output module arranged to output an audio signal to be heard by the user,
wherein properties of the audio signal are adjustable based on sleep-related parameters identified in the EEG signal,
wherein the audio output module comprises one or more micro-speakers mounted in the wearable unit, and
wherein the one or more micro-speakers comprise microfiber portions fabricated in the flexible band.

13. The wearable device of claim 12, wherein the flexible band includes a frontal portion for lying over a forehead of the user when worn, and wherein the sensor array comprises a first set of the plurality of sensor elements mounted on the frontal portion.

14. The wearable device of claim 13, wherein the flexible band has a rear portion for lying over a parietal lobe of the user when worn, and wherein the sensor array comprises a second set of the plurality of sensor elements mounted on the rear portion.

15. The wearable device of claim 12, wherein the flexible band is an eye mask or bandana.

16. The wearable device of claim 12, wherein the detector is mounted on a substrate that conforms to a shape of the flexible band.

17. A wearable device comprising:
a flexible band to be worn around a head of a user;
a sensor array mounted to the flexible band, the sensor array comprising a plurality of sensor elements for making electrically conductive contact with a scalp of the user;
a detector arranged to detect voltage fluctuations at each of the plurality of sensor elements caused by electro-encephalographic (EEG) activity of the user and to generate an EEG signal therefrom; and
an audio output module arranged to output an audio signal to be heard by the user, wherein properties of the audio signal are adjustable based on sleep-related parameters identified in the EEG signal,
wherein the flexible band includes a conductive interconnection structure that is encased within layers of fabric that form the flexible band and provides an electrical connection between the sensor array and the detector, and
wherein the conductive interconnection structure comprises a conductive fabric sandwiched between a pair of insulation layers.

* * * * *